United States Patent
Tilles et al.

(10) Patent No.: US 7,405,073 B2
(45) Date of Patent: *Jul. 29, 2008

(54) POINT SOURCE BIOLOGICAL AGENT DETECTION SYSTEM

(75) Inventors: David J. Tilles, Woodstock, MD (US); Gabriel A. DiFurio, Baltimore, MD (US); John C. Schmidt, Baltimore, MD (US)

(73) Assignee: Northrop Grumman Corporation, Los Angeles, CA (US)

( * ) Notice: Subject to any disclaimer, the term of this patent is extended or adjusted under 35 U.S.C. 154(b) by 322 days.

This patent is subject to a terminal disclaimer.

(21) Appl. No.: 10/441,101

(22) Filed: May 20, 2003

(65) Prior Publication Data

US 2004/0063198 A1  Apr. 1, 2004

Related U.S. Application Data

(60) Provisional application No. 60/381,351, filed on May 20, 2002.

(51) Int. Cl.
*C12M 1/34* (2006.01)
*C12M 3/00* (2006.01)
*C12M 1/00* (2006.01)
*G01N 15/06* (2006.01)

(52) U.S. Cl. .............. 435/287.1; 435/283.1; 435/287.2; 422/50; 422/68.1

(58) Field of Classification Search ................ 435/6, 435/91.1, 91.2, 183, 283.1, 287.1, 287.2; 422/50, 68.1
See application file for complete search history.

(56) References Cited

U.S. PATENT DOCUMENTS 3,942,357 A    3/1976  Jenkins (Continued)

FOREIGN PATENT DOCUMENTS

EP    0 169 057    1/1986

(Continued)

*Primary Examiner*—Frank Lu
(74) *Attorney, Agent, or Firm*—Andrews Kurth LLP

(57) ABSTRACT

This invention is directed to a method and apparatus using polymerase chain reaction (PCR) technology for collecting air samples and identifying biological agents in the air sample. The apparatus is capable of detecting transient events such as *bacillus anthracis* in a piece of mail being processed on high-speed mail processing equipment. The system includes apparatus for implementing the following features: particle collection and pre-separation using a collection hood and dry cyclone passive filtration system; continuous particle collection into a liquid sample; automated fluid transfer to a PCR analysis cartridge; and PCR biological identifier apparatus for detecting a bio-agent in a piece of mail following manual transport of the cartridge to the identifier apparatus; retesting of the liquid sample upon various error conditions; confirmation testing upon preliminary positive results; fluid transfer to archive containers at the completion of analysis; and, notification/reporting system to alert designated personnel/organizations upon the occurrence of selected events such as the presence of *bacillus anthracis*.

23 Claims, 6 Drawing Sheets

U.S. PATENT DOCUMENTS

| | | | |
|---|---|---|---|
| 4,213,253 A * | 7/1980 | Gudelis et al. | 434/224 |
| 4,678,752 A | 7/1987 | Thorne et al. | |
| 4,923,491 A | 5/1990 | Lawless et al. | |
| 5,425,263 A | 6/1995 | Davies et al. | |
| 5,849,208 A | 12/1998 | Hayes et al. | |
| 5,855,652 A | 1/1999 | Talley | |
| 6,015,534 A | 1/2000 | Atwood | |
| 6,036,831 A | 3/2000 | Bishop | |
| 6,331,441 B1 | 12/2001 | Balch et al. | |
| 6,337,213 B1 | 1/2002 | Simon et al. | |
| 6,851,459 B2 * | 2/2005 | Squirrell et al. | 141/70 |
| 6,997,374 B2 | 2/2006 | Stradley et al. | |
| 2002/0124664 A1 | 9/2002 | Call et al. | |
| 2002/0126008 A1 | 9/2002 | Lopez et al. | |
| 2003/0004403 A1 | 1/2003 | Drinan et al. | |
| 2003/0058099 A1 | 3/2003 | Lopez et al. | |
| 2004/0010379 A1 * | 1/2004 | Craig et al. | 702/22 |
| 2004/0028561 A1 | 2/2004 | Daugherty et al. | |

FOREIGN PATENT DOCUMENTS

WO  02 29380  4/2002

* cited by examiner

POINT SOURCE BIOLOGICAL AGENT DETECTION SYSTEM

CLAIM OF PRIORITY

This is a Non-Provisional application which claims priority of the filing date of related Provisional Application Ser. No. 60/381,351, filed on May 20, 2002, and which is incorporated herein in its entirety by reference for any and all purposes.

CROSS REFERENCE TO RELATED APPLICATION

This application is related to the invention shown and described in U.S. Ser. No. 10/441,100, entitled "Automatic Point Source Biological Agent Detection System", filed on May 20, 2003, and is assigned to the assignee of this invention.

BACKGROUND OF THE INVENTION

This invention is directed to biohazard detection systems and more particularly to a biohazard detection system for detecting biological agents, such as *bacillus anthracis*, in pieces of mail.

DESCRIPTION OF RELATED ART

The current state of the art in biological agent detection systems includes: (1) automated systems used, for example, by the military that utilize a form of immunoassay technology; and (2) manual systems including bio-identifier apparatus used in laboratories by skilled laboratory technicians. The automated immunoassay systems used by the military have not demonstrated sufficient sensitivity or specificity to be acceptable for use in civilian applications such as mail screening within the United States Postal Service (USPS). Likewise, manual systems that require skilled technicians to perform sample preparation and to interpret test results are impractical in an industrial environment.

A typical bio-detection system in accordance with the known prior art is comprised of the following subsystems: (a) a trigger to detect the presence of a bio-agent and start the sample collection process; (b) an aerosol collector for collecting samples from the air; and, (c) an identifier to identify the specific bio-agent.

In the USPS environment, various bio-detection systems have been tested in connection with Mail Processing Equipment (MPE) but have been found to be unreliable in distinguishing between letters spiked with bacterial spores from uncontaminated letters or letters containing hoax powders.

SUMMARY

Accordingly, it is the primary object of the subject invention to detect an aerosolized biological agent in an aerosol sample.

It is a further object of the subject invention to detect an aerosolized biological agent originating from a piece of mail.

It is another object of the subject invention to provide a biological agent detection system which achieves higher sensitivity and lower false positives (false alarm) rates than current technology.

The subject invention utilizes the polymerase chain reaction (PCR) technology that is particularly adapted for USPS application. The limit of detection for immunoassay based technology is in the range of 10,000 to 100,000 spores per ml of sample. PCR has demonstrated the ability to detect less than 200 spores per ml of sample. This difference in sensitivity is critical, and may make the difference between detecting and missing a lethal threat in the USPS application. Since PCR detects the actual DNA sequence of an agent, it is also, much less likely to cause false positives than the systems based on immunoassay techniques.

This is achieved by a point source biohazard detection system (BDS) which combines automated fluidic transport apparatus with aerosol collector apparatus and biological agent identifier apparatus. The invention includes means for implementing the following features: particle collection and pre-separation using a collection hood or other means capable of collecting emitted particulates from items and dry cyclone passive filtration system; continuous particle collection into a liquid sample; automated fluid transfer to a sample analysis cartridge; and polymerase chain reaction (PCR) type bioagent identifier apparatus for detecting an actual DNA sequence so as to identify a bio-agent when a collected liquid sample is manually taken from an aerosol collector, prepared, and introduced manually into the bio-agent identifier. The system also provides for automatic retesting upon various error conditions; automatic confirmation testing upon preliminary positive results; automated fluid transfer to archive containers at the completion of analysis; and automated notification/reporting system to alert designated personnel/organizations upon the occurrence of selected events.

The biological agent detection system in accordance with the subject invention is not limited to, but is of particular importance to the US Postal Service (USPS) due to the fact that it would enhance the safety of its work force by quickly detecting the presence of toxic biological agents in a mail processing facility. The system would notify facility personnel so that appropriate actions may be taken quickly to contain a threat from biological agents, such as *bacillus anthracis*, in mail being processed at the facility, thereby preventing dispersion of biological agents between USPS facilities and the general public.

The subject approach makes the system operation independent of an optical trigger input. When desirable, however, an optical trigger device may still be used, for example, to create a record of particle concentration spikes that occur during the mail processing window. This record will permit one to identify the contaminated machine and the approximate time the contaminated letter passed the machine after the identifier indicates that a biological agent is present. In the future, if optical trigger reliability improves, the subject system is compatible with the integration of a trigger that operates in parallel with the continuous collection process. In such an implementation, the trigger would be used to alert an operator to transfer a sample for analysis, resulting in a more timely response to an incident.

Further scope of applicability of the present invention will become apparent from the detailed description provided hereinafter. It should be understood, however, that the detailed description and specific example, while disclosing the preferred embodiment of the invention, is provided by way of illustration only, since various changes and modifications within the spirit and scope of the invention will become apparent to those skilled in the art.

BRIEF DESCRIPTION OF THE DRAWINGS

The present invention will become more fully understood from the detailed description provided hereinbelow and the accompanying drawings which are given by way of illustration only, and wherein.

DETAILED DESCRIPTION OF THE INVENTION

System Overview

Figure 1:
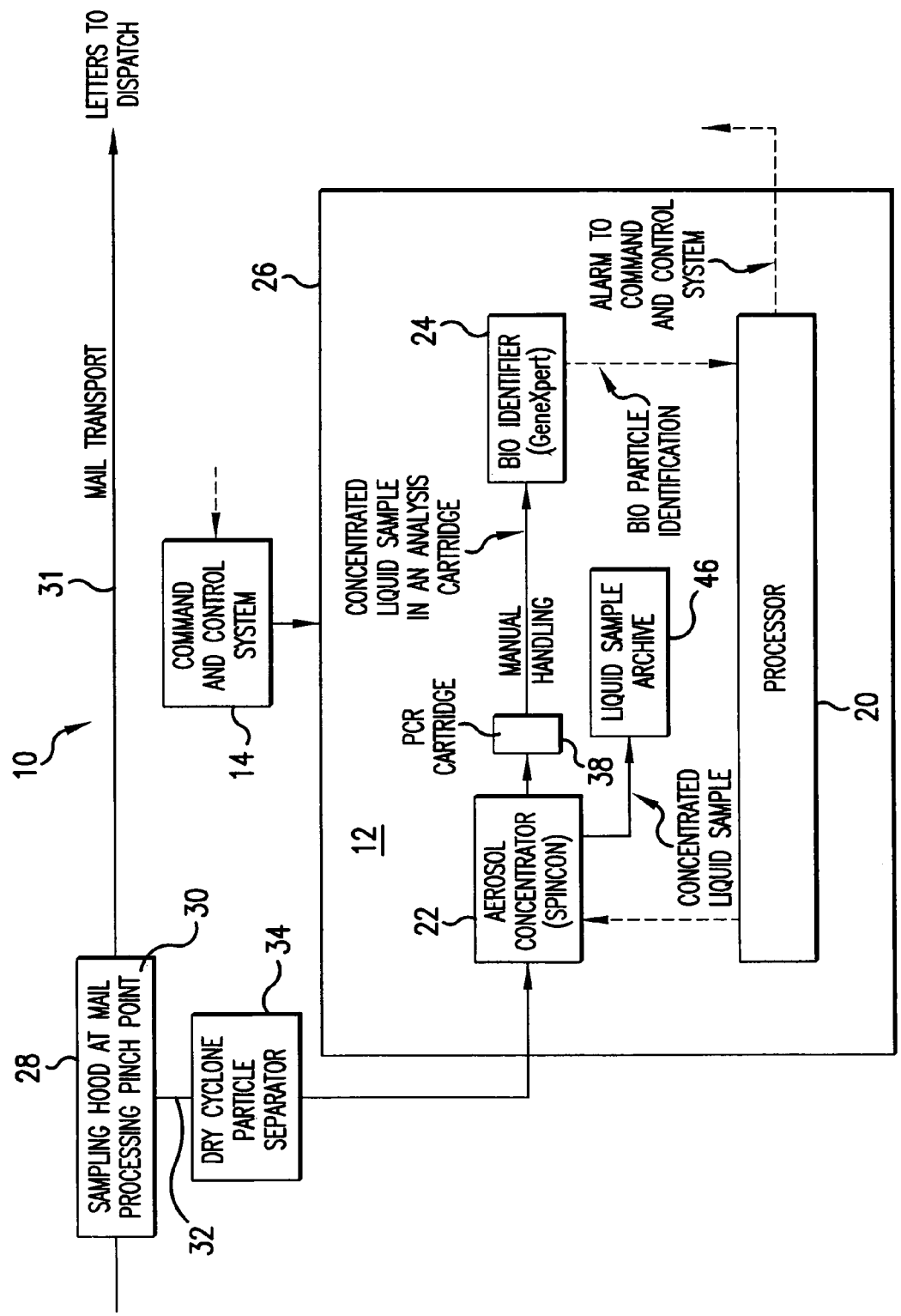
FIG. 1 is a system block diagram illustrative of a bio-detection system in accordance with a preferred embodiment of the subject invention.

Referring now to the various drawing figures where like reference numerals refer to like components throughout, shown thereat is a biohazard detection system (BDS) 10 for a mail processing facility, such as, but not limited to a United States Postal Service (USPS).

Figure 2A:
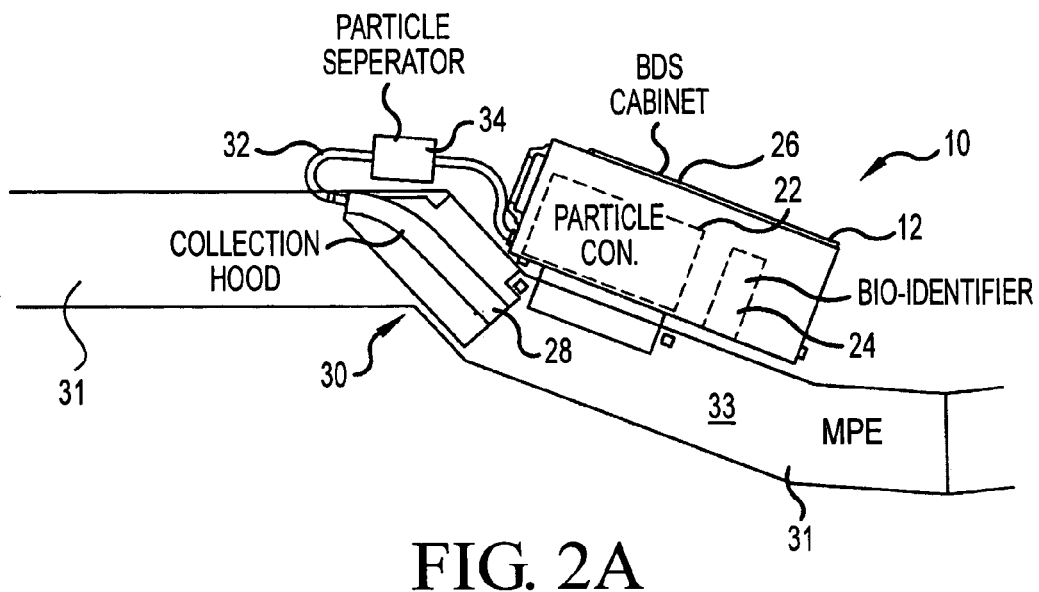
FIGS. 2A, 2B and 2C are illustrative of the location and mechanical details of two types of aerosol sampling systems located at a mail processing facility.
Figure 3:
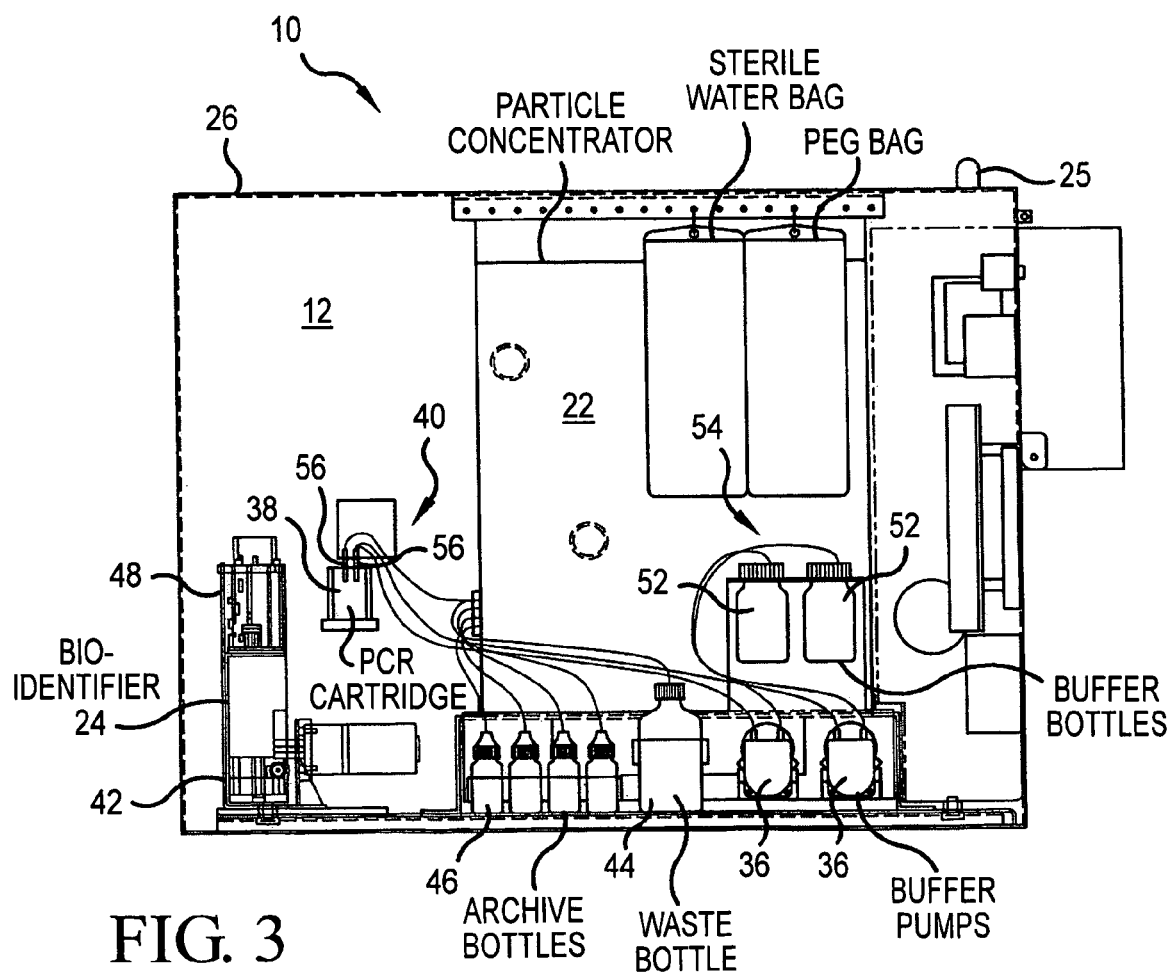
FIG. 3 is a system block diagram further illustrative of the apparatus located in a monitor unit shown in FIG. 1.

In FIGS. 1, 2 and 3 and the BDS 10 is comprised of a single monitor unit 12; however, more than one monitor unit can be employed depending on the needs of the particular facility. In either case, one or a plurality of the monitoring units 12 is under the control of a central site command and control unit 14 (FIG. 1). The monitor unit 12 can be coupled to the site command and control unit 14 either by way of a hardwired network or an RF link, as desired. Each monitor unit 12 includes two major sub-systems under the control of a machine control processor 20, namely: an aerosol collector/concentrator and fluidics transfer sub-system 22 and a bio-identifier sub-system 24 which are located in a cabinet shown by reference numeral 26.

Figure 2B:
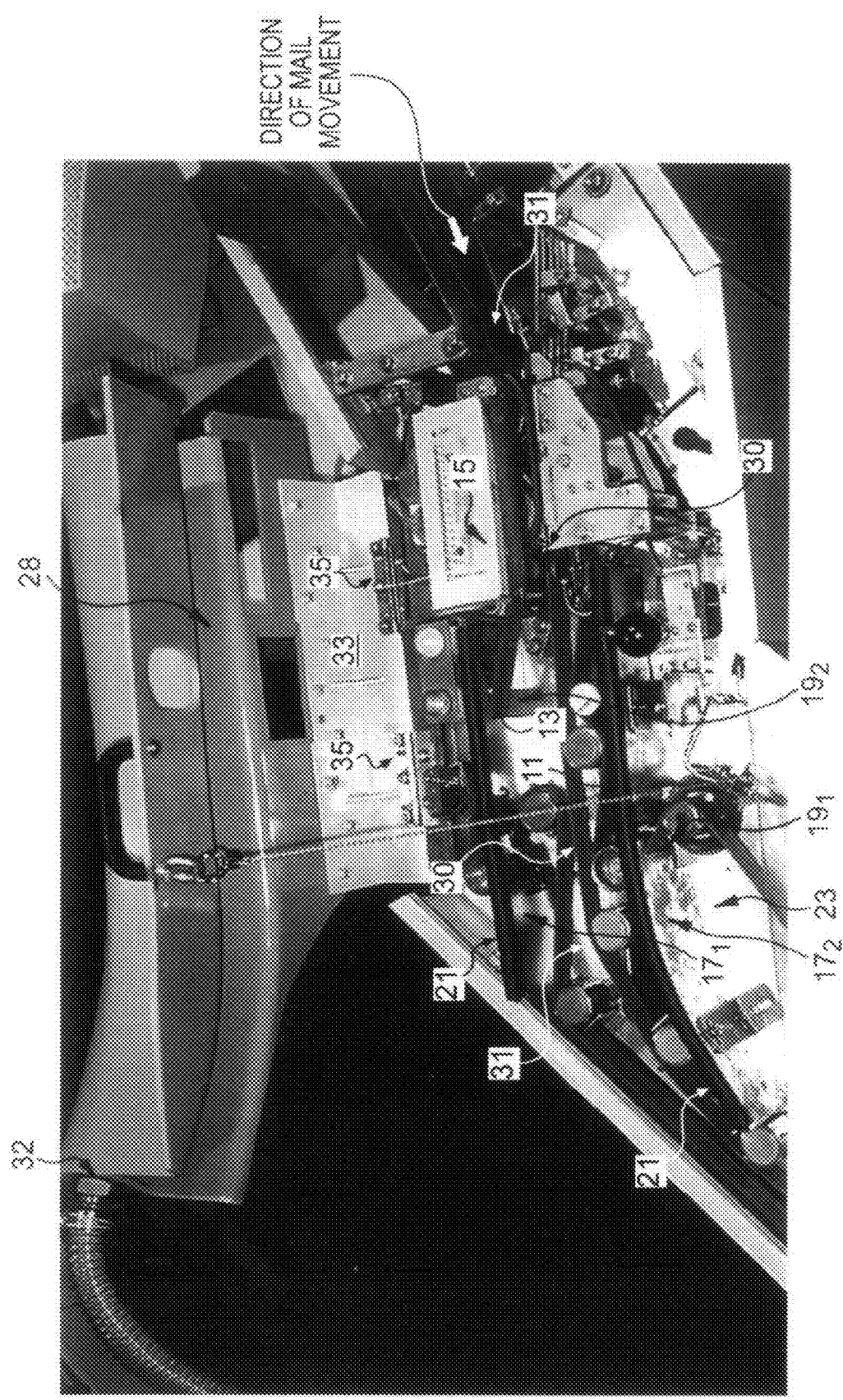

In addition to the monitor unit 12, the subject BDS 10 as shown in FIG. 1 includes sampling and collection apparatus comprising a hood 28 or a shroud (not shown), referred to hereinafter simply as a hood, for sampling the air and collecting an aerosol sample of particles of an aerosolized biological agent at a monitored location along a mail transport path 31, and including pinching apparatus, to be described, located at a pinch point 30 along the mail transport path 31 and under the hood 28 of high speed automated mail processing equipment 33 (MPE) as shown in FIG. 2A. FIG. 2B shows structural details of the hood 28 which is hinged and covers a portion of the transport path 31 which is part of a facer/canceller system used for canceling letters. Mail processing equipment, including facer/canceller apparatus, normally transports mail items along the transport path 31 by pinching letter items between two opposing moving belts 11 and 13 of a dual belt mail transport assembly, wherein mail pieces are typically transported in a vertical position. At the pinch point location 30, underlying the hood 28, mail being transported along the transport path 31 of the facer/canceller mail processing equipment is converted from a loosely held, non-singulated flow of mail pieces to a singulated flow by a singulator device 15 which pinches an individual mail piece and pulls it away from the non-singulated items. The location and construction of the sampling hood 28 which overlays the pinch point 30 in a lowered position, is based upon testing that demonstrates that particles contained in mail pieces are expelled when the mail piece is pinched by the singulator 15 as well as by the belts 11 and 13 following the singulator 15. The hinged sampling hood 28 is configured to capture virtually all of the particles expelled from the envelope of the mail piece in the immediate vicinity of the pinch point 30 by virtue of the structure additionally including a pair of vertical side panels $17_1$ and $17_2$ located on either side of the mail path forming a closed mail transport passage for the belts 11 and 13, and the individual pieces of mail being transported thereby. The side panels $17_1$ and $17_2$ have cut-outs $19_1$ and $19_2$, respectively, to allow the mail transport belts 11 and 13 to pass therethrough while still capturing the majority of the particles expelled from the mail piece. A gasket 21 is located at the top of the side panels $17_1$ and $17_2$ to interface with the hinged hood 28. The hinged hood 28, when in the lowered position (not shown), is the final element of a tunnel consisting of the baseplate 23 of the mail processing equipment 33, the two side panels $17_1$ and $17_2$ and the hinged hood 28. The hinged hood 28 includes an arcuate shape so as to guide aerosol particles to the entry point of a sampling hose 32 located at the far end, i.e., the downstream end, of the tunnel. The tunnel has been sized so that the sampling volume of the aerosol concentrator (nominally 450 liters per minute) creates sufficient face velocity of the air in the tunnel so that particles in the inhalable threat region (up to 10 microns) will not settle out inside the tunnel, but remain aerosolized. In addition, the motion of letter mail through the tunnel creates airflow through the tunnel and mixes the air so that the particles do not settle out within the tunnel and are available for sampling at the entry point to the sampling hose 32 leading to the particle separator 34 and aerosol concentrator 22 (FIG. 3A). The hood 28 is hinged as shown in FIG. 2B so as to allow it to be lifted up and out of the way to clear mail jams, for example, that sometimes occur at the singulator 15.

Figure 2C:
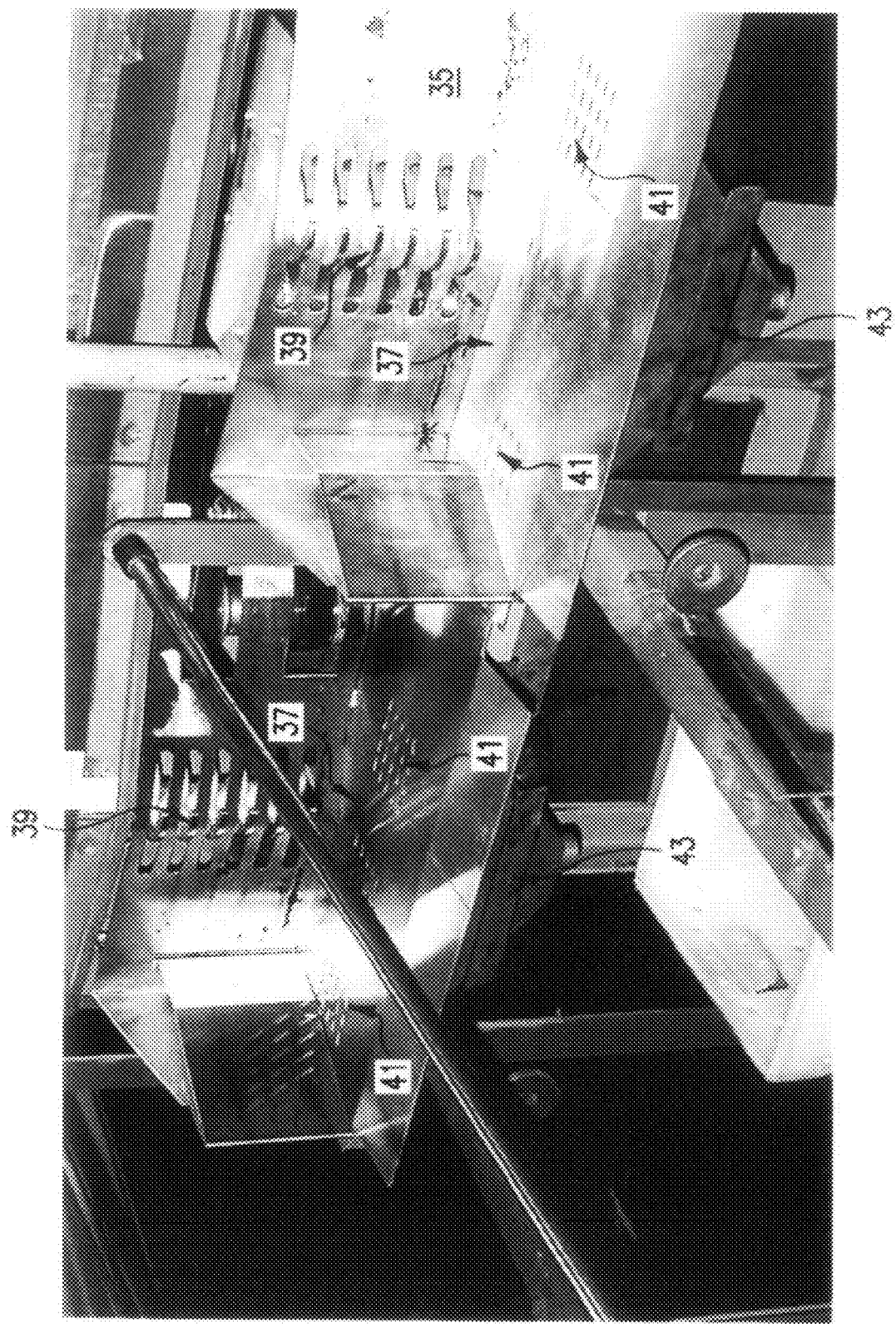

Alternate sampling systems have also been designed for other pieces of mail processing equipment. In particular, a manifold system 35 has been designed for a flats canceller. FIG. 2C shows the stacker area 37 of a Model 15 Flats Canceller used by the USPS in canceling flats mail. This manifold system creates a downward airflow in the stacker area 37 of the flats canceller. After the flats are cancelled, they are stacked or placed back into an organized group so that they can be placed into a container and transported to downstream processing. As the flat sits in the stacker, a rotating arm 39 pushes against the flats to keep space available for the next flat coming from the canceller. The rotating arm 39 repeatedly impacts the flats sitting in the stacker, which has been shown to cause particles in the flat mail piece to be expelled. These expelled particles are then drawn down through the perforations in the baseplate(s) 41, into the suction manifolds 43, and on through the remaining components of the system. Similar sampling hood or sampling manifold designs have been developed for other types of mail processing equipment.

The first time that a letter, for example, is pinched at pinch point location 30, air is pushed out of the envelope. If there are particles inside the envelope, some will come out of the envelope at that point. Sampling is performed within the hood 28 situated at the location of the pinch point 30 by capturing the particles that are emitted at the pinch point. The design of the hood 28 and the sampling rate of the air collector are matched so that the air inside the hood is sampled at a rate that will evacuate virtually all of the particles present along this portion of the transport. This has two benefits, namely: it reduces the dust that is created by the mail processing operation, thereby reducing the cleaning maintenance required, and it ensures that as many target particles as possible are captured for analysis.

After the particles are captured, they are sent via a hose 32 through a dry cyclone 34, that utilizes the particle aerodynamic size to separate out larger particles, from those that are in the inhalable size range, and therefore pose the highest threat to human health. This cleans up the aerosol sample, and prevents large dust and fibrous particles from clogging the downstream equipment and interfering with the bio-detection process. The large particles are captured in a container, not shown, and disposed of. No filter media that can become clogged with dust is utilized.

The air from the pinch point 30 can, when desired, be continuously monitored by an optional particle counter, not shown, which determines the number of particles per second in a number of size ranges passing by the air sample point. Such an option would provide a historical record of particle count that may be useful in assisting someone in identifying the contaminated mail sorting machine and the approximate time a contaminated letter passed through the machine in the event the monitor unit described below detects a biological agent. If a spike is detected in the counted particles with characteristics that match the target of interest, such as *bacillus anthracis*, the system can also use this event to automatically trigger a sample analysis process to be described hereinafter. Particle characteristics evaluated can include count, size, shape, and fluorescence signature, among others. It is also possible to use a mass spectrometer, not shown, as a trigger.

As noted, a BDS system 10 in accordance with the subject invention normally operates without a particle counter 28.

Referring now to FIG. 3, an aerosol particle collector/concentrator assembly 22 is preferably a SpinCon® system and constantly draws an air sample from the sampling hood 28 and the dry cyclone particle separator 34 and impinges the sample into approximately 10 ml of liquid located in a glass collector, not shown. At selected times under the control of the machine control processor 20 (FIG. 1), the solution is pumped out of the collector to a reservoir where it is optionally mixed with a buffer liquid by one or more buffer pumps 36. A fraction, nominally 2 ml, of the mixed sample is automatically pumped into a polymerase chain reaction (PCR) cartridge 38 at a fill station 40. Additional buffer and treatment solutions may also be added, when desired, to the cartridge 38 at the fill station 40.

An operator then manually transfers and inserts the cartridge 38 in the door 42 of the bio-identifier apparatus 24, preferably comprising a GeneXpert™ instrument that implements a (PCR) analysis capable of determining with a high degree of reliability if any particles in the liquid sample comprise a biological agent. The GeneXpert™ apparatus 24 automatically processes the sample and performs a PCR analysis to determine if one or more biological agents are present. If the test result is either positive for the agent(s) under test, or non-determinate, indicating that certain internal controls included in the PCR analysis did not perform correctly, an additional test is performed using an additional fraction of the original sample and a new cartridge 38. At the completion of the analysis, the remaining sample is transferred from the reservoir into a waste bottle 44, or to archive bottles 46 for later laboratory confirmatory analysis and retention as evidence. The system can optionally individually archive all samples or only those that generate a positive test result. The bio-identifier apparatus 24 is controlled by the central site command and control system 14 (FIG. 1).

The BDS 10 continuously collects aerosol particles from the pinch point 30 along the mail transport path 31 of the MPE as shown in FIG. 1. Periodically, the liquid sample containing the particles will be analyzed using an automated PCR test by the operator manually retrieving a cartridge 38 and placing it in the bio-identigier 24. This initial analysis is termed a Preliminary, or Screening Test. If the test is negative for agents of interest, no action is necessary, and the facility operations will continue as usual.

Figure 6:
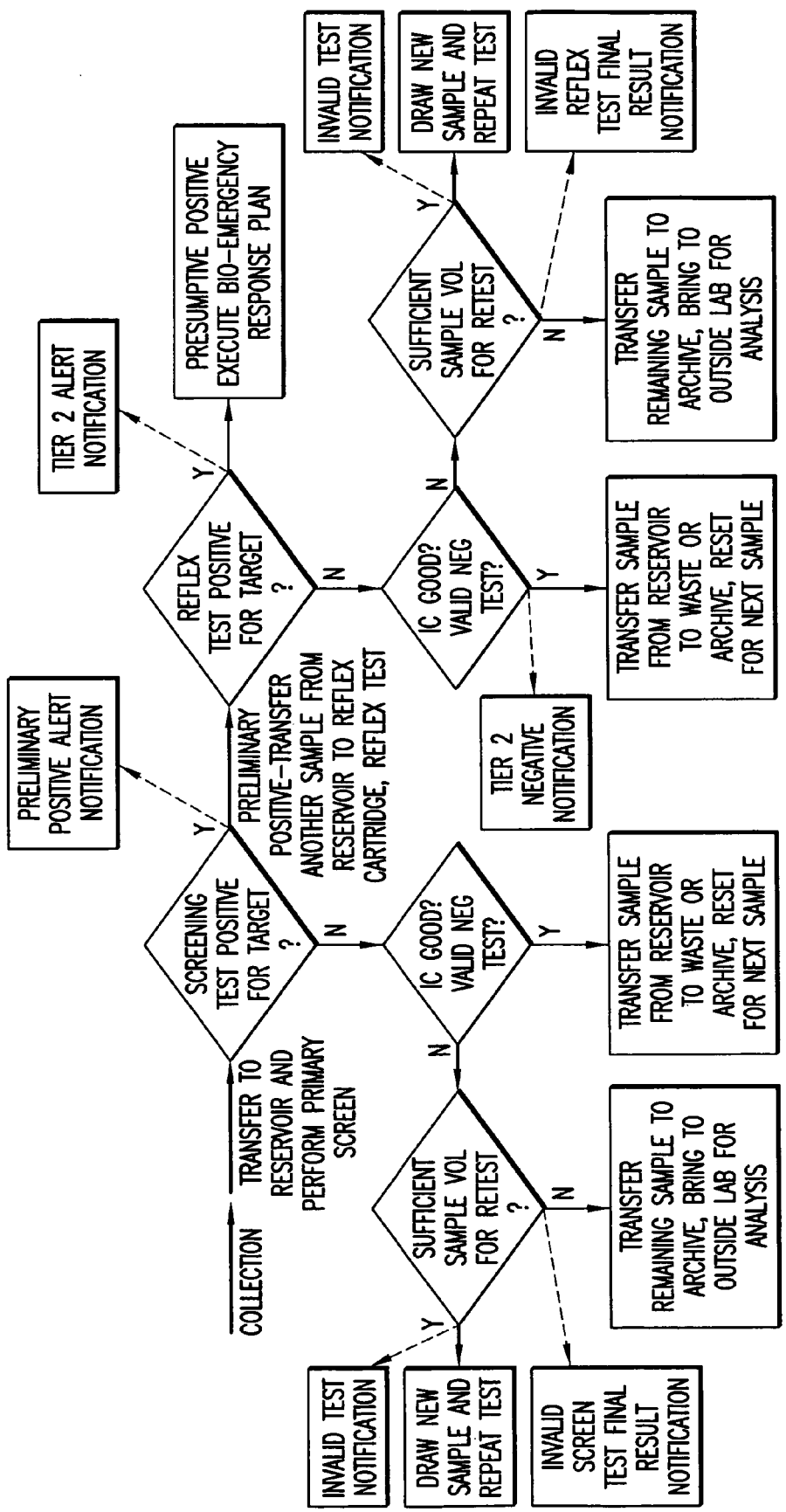
FIG. 6 is a diagram illustrative of a flow chart of the operation of the bio-detection system in accordance with the subject invention.

If the result of the test is a "preliminary positive", the system will automatically perform a confirmation (Reflex)-test, optionally utilizing a criteria that is independent from the Screening Test, such as a secondary gene sequence from the target organism. Preliminary positive and confirmation test results are reported to a Visibility/Incident Response network. The results can be used to make the most appropriate decisions regarding personnel evacuation and emergency response scenarios, and further analysis of the archived sample using an outside laboratory. FIG. 6 is illustrative of this sequence of events.

System Details

Site Control

Considering the subject invention in greater detail, the site command and control system 14 (FIG. 1) provides coordination and communication of the components in the biohazard detection system (BDS). The command and control system 14 is designed to: (a) provide a single user interface to the entire bio-detection system; (b) allow the user to quickly determine the status of all components associated with the system; and (c) accept input to change parameters which allow for the configuration changes At its most basic level, the command and control system 14 provides an alarm when a "positive" reading has been obtained from the bio-identifier 24. The system 14 includes a control computer, not shown, that provides an interface to the operators and supervisors about the status of the overall system. This computer is furthermore networked to all sensor devices (like particle counters) and to each monitor unit. 12 where a plurality of monitor units are located at a particular site. The system 14 provides the higher level data collection of statistics of each component that is necessary for reports and on screen visibility. The system 14 also provides data about the test results from the bio-identifier 24.

Machine Control

The monitor unit 12 also contains a machine control processor 20 that sends and receives commands to and from the control computer of site command and control system 14. The control processor 20 performs machine control functions which: (a) controls the fluid interface between the collector/concentrator sub-system 22 and the bio-identifier sub-system 24; and (b) responds to any faults or alarms therefrom. Machine control functionality provided by the processor 20 has been separated from the command and control 14 because the machine control processor 20 handles time critical commands that affect the operation of the system components in the monitor unit 12.

Aerosol Collector/Concentrator

Figure 4A:
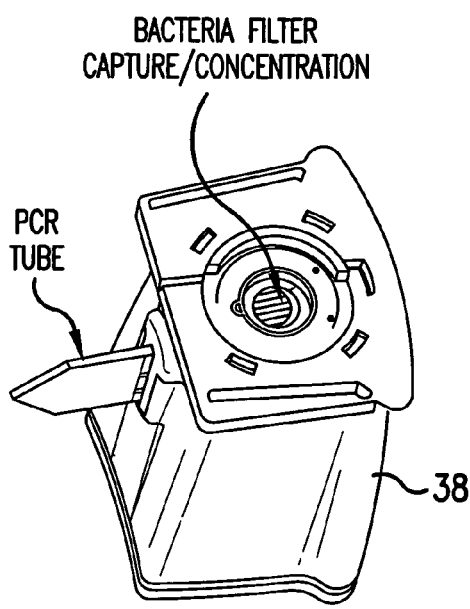
FIGS. 4A, and 4B are perspective views respectively illustrative of top and perspective views of a PCR sample cartridge utilized in connection with the apparatus shown in FIG. 3.
Figure 4B:
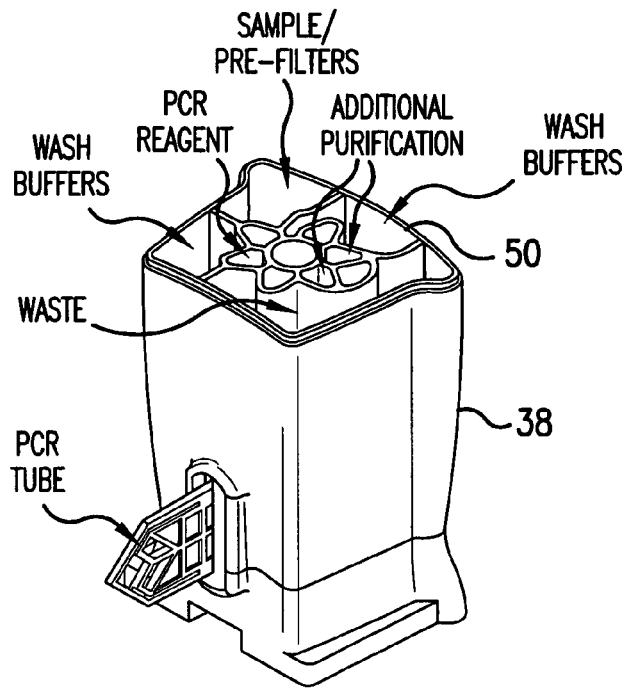

Several different types of aerosol collector/concentrators 22 can be used with the subject system, however, the preferred embodiment of this equipment comprises a proprietary SpinCon® system developed by Midwest Research Institiute (MRI). The SpinCon® apparatus 22 is an efficient device proven to be ideally suited for a broad range of advanced air sampling requirements, including the collection of bio-aerosols, particulate matter, and soluble vapors. The primary sample collection component of the SpinCon® system 22 consists of a vertical glass tube, not shown, open on the top end, with a nearly tangential, vertical slit cut into the side and is called the contactor. Fluid is placed in the contactor and air is drawn through the slit and out through the open top end of the contactor. The slit acts like a venturi/air blast atomizer; as the air passes through the slit, it speeds up and then impacts the spinning fluid in the contactor forming a wet cyclone. The collection fluid then atomizes into many small droplets, greatly increasing the surface area in contact with the air. These droplets then begin to follow the air path. The slit is only nearly tangential so the air path is across a chord of the contactor's circular cross-section. At this time, particles in the air are picked up by the fluid. As the air and droplets reach the other side of the contactor, the droplets impinge on the wall and the fluid flow is re-formed. The same fluid is re-atomized over and over, thus causing the concentration of particles in the fluid to increase linearly with time. The spinning fluid in the contactor only covers 30 to 40 percent of the slit, which is why only 30 to 40 percent of the air is sampled that is pulled into the unit.

The SpinCon® system 22 is very effective in collecting biologicals (sizes 1-10 microns) as well as many types of smaller particles and even chemicals (agglomerated sizes <1 micron.) This is due to the atomized state of the fluid at the point of collection; the massive surface area collects the larger particles, while Brownian motion, which governs the motion of small particles, enables the smaller particles to be picked up in the fluid.

Bio Identifier:

As noted above, two technologies are commonly used in the detection of biological warfare agents: namely, (1) immunoassay and (2) polymerase chain reaction (PCR). Immunoassay technology is based on the specific interaction of antibodies with pathogen. This interaction is usually detected optically or electrochemically. PCR, on the other hand, directly detects the DNA sequence of an agent.

PCR technology has been selected for the subject invention because of its superior sensitivity and specificity. The limit of detection for immunoassay based technology is in the range of 10,000 to 100,000 spores per ml of sample. PCR has demonstrated the ability to detect less than 200 spores per ml of sample. This difference in sensitivity is critical, and can make the difference between detecting and missing a lethal threat, for example, in a USPS application. Since PCR detects the actual DNA sequence of an agent, it is also much less likely to cause a false positive than the systems based on immunoassay techniques. Also, sequences associated with the actual virulence properties of the organism can be targeted. This will also be critical for a USPS application, since a false positive may result in a major financial loss if it causes an unnecessary shutdown of a mail processing facility.

PCR techniques have become recognized as one of the most reliable laboratory techniques, along with culture methods, to validate immunoassay and other field screening techniques. In recent years the development of real time PCR techniques have allowed the reaction to be performed in 30 minutes or less. This enables the use of PCR in field applications where rapid results are required. However, all current PCR methods require sample preparation to remove inhibitors (such as the humic acids from soil) from the sample that may result in a false negative and add reagents necessary to run PCR. This sample processing requires significant laboratory operations that USPS personnel could not reliably perform in the current mail processing facilities. For this reason, most PCR systems, cannot be used in the USPS application or similar industrial environments.

The subject invention uses a PCR bio-identifier system that completely automates both sample processing and detection processing and comprises a GeneXpert™ system developed by Cepheid of Sunnyvale, Calif. This system consists of two components, a disposable multi-chamber cartridge 38 such as shown in FIGS. 4A and 4B and a PCR analysis instrument 48. The aerosol collector 22 described previously automatically loads a liquid sample into a GeneXpert™ cartridge 38 at the fill station 40 (FIG. 3) which is then manually transported to the GeneXpert™ instrument 48 by an operator. The GeneXpert™ instrument 48 then automatically performs the entire sample preparation, PCR amplification, and results analysis with no additional intervention by the operator. The fluid sample and liquid reagents are automatically transported from one chamber 50 (FIG. 4B) to another within the disposable cartridge 38 as shown in FIG. 5 where fluids are mixed, molecules and organisms are separated, purification is accomplished, filtering is performed, lysing is completed, all automatically with no operator intervention. The GeneXpert™ instrument 48 automates all fluidic processing steps.

The key advantages of the GeneXpert™ bio-identifier instrument 48 utilized in the subject invention are:

(a) on-board PCR reagents—The critical PCR chemicals (or reagents) are "on-board" the GeneXpert™ cartridge 38, and are installed at the factory. Thus, the operator does not need to handle the sensitive reagents. Since they are pre-mixed and lyophilized at the factory, there is no chance for mistakes in mixing by an operator and thus there is no need to refrigerate the cartridges;

(b) spore lysing—The GeneXpert™ instrument 48 incorporates an ultrasonic lysing region which actually cracks open the spore, releasing the DNA from inside the organism, in about 15 seconds. This capability does not exist with any other known DNA analysis system. Systems that do not lyse the organism cannot guarantee that the DNA from the organism is actually available for PCR detection. Such systems that do not lyse can readily report a false negative, especially for spores such as *bacillus anthracis;*

(c) inhibitor removal—Many types of common biological samples, including common dirt, contain extraneous chemicals that impede the PCR detection reaction. The presence of these inhibiting chemicals can cause PCR reaction to fail, thereby resulting in a false negative. The GeneXpert™ instrument 48 captures the spores, then actually washes them with a PCR-compatible buffer solution to remove any potential inhibiting chemicals prior to performing the PCR reaction itself. Systems which do not remove inhibitory chemicals can easily report a false negative;

(d) pathogen concentration—Pathogens can be present in raw samples or can be released into the air at extremely low concentrations, yet still remain infectious. In order to ensure that such pathogens can be detected with the highest possible sensitivity, the GeneXpert™ instrument 48 actually extracts and concentrates the spores from a relatively large original sample volume (up to several mL) into a small PCR reaction tube of the cartridge 38. Other PCR instruments simply take a small portion of the available liquid sample and perform PCR on this small portion. As a result of the concentrating ability of the GeneXpert™ apparatus 48, the system routinely achieves a sensitivity at least 10 times better than competitive products which do not concentrate the sample;

(e) no environmental contamination or cross contamination—Since all the fluidic activity for PCR detection occurs automatically and is completely contained inside the GeneXpert™ cartridge 38, it is impossible for the GeneXpert™ instrument 48 to inadvertently contaminate the environment or the instrument with PCR product. For example, if a specific sample tests positive for *bacillus anthracis*, the resulting liquid is now very concentrated with *bacillus anthracis* DNA. In a manual-based system, small portions of this liquid could escape into the environment as liquids are pipetted or moved from tube to tube. If *bacillus anthracis* DNA from the PCR reaction escapes into the environment, this could become a source of contaminating DNA which could cause a false positive during subsequent tests. Since fluids are always retained inside the GeneXpert™ cartridge 38, such potential false positives are eliminated;

(f) robust reaction tubes—GeneXpert™ cartridges 38 and integrated reaction tubes 50 as shown in FIG. 4B are all plastic. In contrast, other products have glass reaction tubes. These glass tubes easily break. When they do break, they not only present a maintenance, service, and reliability issue, but they can also contaminate the environment with *bacillus anthracis* DNA, again providing a source for potential false positives during subsequent tests; and, (g) multi-target detection—When using PCR, the definitive identification of *bacillus anthracis*, for example, requires the detection of two different DNA segments. The GeneXpert™ instrument 48 has a versatile multiplexing capability in that multiple DNA targets can be detected simultaneously in the same PCR reaction tube 50 of a cartridge. Multiplexing capability is a critical feature for DNA analysis and pathogen detection. For example, with the GeneXpert™ system, a single test or analysis for up to four agents can be performed within a single disposable cartridge 38. Alternatively, a completely confirmatory test for an agent such as *bacillus anthracis* can be performed within a single cartridge 38. This assay would include three probes for the three different DNA segments and one probe for an internal control. With the GeneXpert™ instrument 48, this can be done in a single test cartridge 38. Finally, most robust PCR chemistries require an internal "control" DNA sequence. This control sequence is amplified and detected along with the "target" DNA (such as *bacillus anthracis*) to assure that the PCR chemistry is performing properly—basically a validation or quality check. The GeneXpert™ instrument 48 has four independent optical detection channels. Accordingly, these advanced, but necessary, multiplexing chemistries can be utilized for: (1) multiple pathogen detection; (2) confirmatory testing; and/or (3) test quality/validation control.

In current PCR methods, separate positive and negative controls must be run to assure reagent integrity or successful removal of inhibitors during sample preparation. A new internal control scheme that eliminates the need for these external controls is achieved by a unique combination of an internal control and probe integrity check called probe check. The internal control consists of a piece of DNA whose sequence is different than the target DNA and a corresponding probe that is included in the PCR bead. The internal control is co-amplified along with the test reaction and is used to assure that the reagent is functional and that PCR inhibitors have been successfully removed during sample preparation.

System Operation

In a United States Postal Service (USPS) installation, the biological agent detection system (BDS) in accordance with the subject invention is deployed on mail processing equipment (MPE). The operation of the subject bio-detection system is controlled by the machine control processor 20, and its operation is synchronized with the operation of the monitored MPE so that it is only allowed to operate when the BDS collector/concentrator is operational. The flow chart shown in FIG. 6 is illustrative of the operational sequence.

Prior to collecting samples, the BDS must be initialized and prepared for data collection. The following describes the tasks involved: (1) start-up of site command and control system; (2) set collection parameters. The collection parameters include the setup for each run in sequential order for the tour. The run setup will indicate the machine ID sample number, start time, stop time, and the assay description. The assay description is associated with a command sequence used by the GeneXpert™ instrument 48 to perform the PCR analysis. The command sequences are stored locally in the machine control processor 20 (FIG. 1). The supervisory system 14 will have the capability to download a new assay description and associated command sequence to the machine control processor; and, (3) powers up the BDS monitor 12. The system will automatically perform a communications and systems status check; rinse and prime the fluid lines; and indicate whether fluid levels are low.

At the specified start time, the BDS initiates the air collection process. This enables the collector/concentrator sub-system 22 to start operation. An indicator 25 on the cabinet 26 (FIG. 3) provides an indication that the system is active.

Air is then sampled from the output of the air collection hood 28 where it is routed via tube 32 which is a grounded anti-static tube to the dry cyclone pre-separator 34 that is designed to eliminate particles that are larger than the inhalation threat range of 1-10 microns.

From the dry-cyclone 34, the sampled aerosol is routed to the SpinCon® collector/concentrator apparatus 22 which, as noted above, impinges the air into a small volume of liquid. The aerosol collector operates at a flow about 450 lpm. As air passes through the unit, cyclonic mixing transfers a high portion of the target particles into the liquid. The liquid medium remains in the collector/concentrator 22 to continuously concentrate the target particles into the liquid. At the start of the collection process, 10 ml of sterile water is injected into the system. During the collection, the water level is monitored, and evaporated water is replaced by injecting makeup water to maintain to 10 ml sample volume.

At a planned "stop time" or in response to a trigger input, the machine control processor 20 sends a signal to the collector/concentrator 22 to transfer a liquid sample out for analysis. The aerosol collection process and facer/canceller operation are paused while the sample is transferred into one or more bottles 52 of a collection reservoir 54 (FIG. 3), and the collector/concentrator 22 is then refilled to start the next collection window.

As the liquid sample is transferred into the reservoir 54, it is mixed with a solution containing additives that minimize PCR inhibition. The liquid sample is then allowed to sit in the reservoir for a time, e.g., approximately two minutes, to allow thorough mixing of the additive solution, and allow any large particles to settle to the bottom of the reservoir bottle(s) 52.

Before or after the liquid has settled, an operator places a PCR cartridge 38 in position at the "liquid fill" station 40 in the BDS cabinet 26 as shown in FIG. 3. The three needles at the liquid fill station 40, two of which are shown by reference numerals 56 and 58, pierce a seal on the top of the cartridge 38, and allows the sample and wash buffer solutions to be added to the appropriate cartridge chambers. The liquid transfers are performed utilizing the pumps 36. Once the sample transfer is complete, an operator takes the cartridge 38 and manually places it in the GeneXpert™ instrument 48, whereupon the sample analysis process is started. Although the process of placing the cartridge 38 in the liquid fill station 40 and, later, in the GeneXpert instrument 48, is described herein as being manually performed, it will be appreciated that these operations can be automated, for example using an automated cartridge handling system as described in related application Ser. No. 10/441,100, filed on even date herewith.

Figure 5:
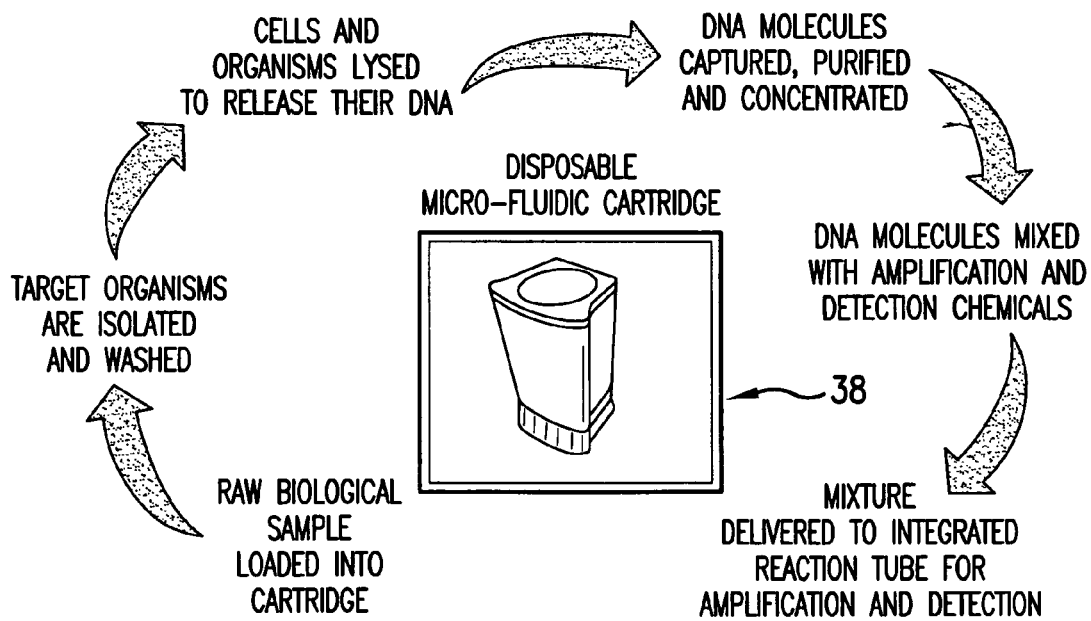
FIG. 5 is a diagram illustrative of the operation performed in the sample cartridge shown in FIGS. 4A and 4B.

Following insertion of the cartridge 38 into the GeneXpert™ instrument 48, an automated sample preparation process begins. The sample is concentrated, washed, sonicated, mixed with the PCR reagents, and moved into a reaction tube 50 (FIG. 4B) for PCR thermal-cycling as shown in FIG. 5. Each of these steps, along with the parameters that control the PCR analysis itself, is elaborated in an assay file that is specific to the test being performed.

Tests

After the sample preparation steps are complete, PCR thermal cycling analysis begins. The primary PCR test is called a Screening Test. This test targets one or more gene sequences for each of the organisms of interest. In addition to the target organisms, the Screening Test also includes an internal control signal that provides a built-in positive control that the PCR reaction has proceeded properly. As the PCR thermal cycles are performed, the fluorescence signals in the cartridge reaction chamber are monitored and analyzed on each thermal cycle using an algorithm that analyzes the shape of the PCR growth curve, including features such as its cycle threshold and endpoint to determine whether the PCR result indicates the presence of the target organism.

(Screening Negative)—In normal conditions, the test results of the Screening Test are negative (N). The test results are sent to the site command and control system 14 (FIG. 1) where the results are logged. The test cartridge 38 is manually removed from the GeneXpert™ instrument 48. The remaining liquid sample in the reservoir bottle(s) 52 is transferred to one of archive bottles 46. or optionally to a waste bottle 44 if the "archive all" parameter is turned OFF. The SpinCon® reservoir 54 is then available for the next sample.

(Screening Positive/Preliminary Positive)—If the PCR bio-identifier instrument 48 detects a positive (Y) Screening Test result, the results are sent to the site command and control system 14, where notifications are sent out according to a prescribed notification and response scenario and a Reflex Test is next performed as will be described hereinafter.

(Screening Process Error/Inhibition)—If the PCR bio-identifier instrument 48 detects an invalid screening result, the test results are also sent to the site command and control system 14, where notifications are sent out again, according to a prescribed notification and response scenario. The system has the capability of utilizing an alternate assay for the repeat test based on the nature of the error on the original screening test. If, based on the background fluorescence, it appears as if there was a bead rehydration or other processing problem, a portion of the archived sample will be utilized to repeat the same assay in a new cartridge 38. If the error appears to be an inhibited sample, a portion of the archived sample will be utilized to perform a slightly modified assay. This assay will: (1) perform additional washes; (2) utilize a higher level of dilution; and (3) adjust the positive detection thresholds based on the modified dilution.

(Reflex Test)—In response to a positive (Y) Screening Test result, (a) the site command and control system 14 will send out Preliminary Positive notifications to the designated contact list, (b) an operator will manually retrieve the cartridge to be used for the Reflex Test, and transport it to the fill station 40 where a fraction of the sample remaining in the reservoir and buffer solutions are transferred into it, and depending on the agents to be tested for, the Reflex Test may simply consist of a repeat of the Screening Test, or it may be performed on a special "reflex" cartridge 38' containing primers for alternate genetic sequences, (c) the appropriate assay for the reflex cartridge is selected, and (d) the reflex cartridge 38' will then be automatically loaded into the GeneXpert™ instrument 48 and a Reflex analysis will be performed.

(Reflex Negative)—The system will transfer the remaining liquid sample into an archive bottle 46. For a negative (N) Reflex Test result, no site alarms or emergency response action are initiated, the GeneXpert™ test results are sent to the site command and control system 14, where the results are logged and test result notifications are sent out. The original screening cartridge, the reflex cartridge, and the archive tube are manually retrieved from the system and saved in refrigerated storage for further analysis to determine the cause of the preliminary positive.

(Reflex Process Error/Inhibition)—For a Reflex Process Error/Inhibition result, no local alarms or emergency response actions are initiated, the test results are sent to the site command and control system 14, where the results are logged and notifications are sent out according to a prescribed notification and response scenario. Another reflex test can be performed, as long as sufficient sample is available.

(Reflex Positive)—The system will transfer the remaining liquid sample into an archive bottle 46. For a positive (Y) Reflex Test result, the GeneXpert™ test results are sent to the site command and control system 14, where the results are logged and test result notifications are sent out. The site emergency response plan is put into effect.

Thus what has been shown and described is a unique biohazard detection system for detecting toxic biological agents, particularly *bacillus anthracis*, in a facility which, for example, handles and processes items, such as mail.

The detailed description provided above, however, merely illustrates the principles of the invention. It will thus be appreciated that those skilled in the art will be able to devise various arrangements which, although not explicitly described or shown herein, embody the principles of the invention and are thus within its spirit and scope.

What is claimed is:

1. A biohazard detection system for detecting biological agents in pieces of mail transported by a mail sorting apparatus comprising a mail transport path, said biohazard detection system comprising:

a collection apparatus comprising a hood or shroud, and a mail pinching apparatus located under said hood and used for causing particle expulsion from mail transported along the mail transport path, said collection apparatus collects an air sample expelled from the mail by said mail pinching apparatus;

a concentrator apparatus connected to said collection apparatus and used for producing a liquid sample of said air sample;

a fluidics apparatus connected to said concentrator apparatus and used for delivering a portion of said liquid sample from said concentrator apparatus to a cartridge type receptacle;

a biological agent identifier apparatus used for receiving said receptacle, when transported thereto, and used for analyzing said liquid sample in said receptacle for a biological agent; and a control apparatus used for providing control of said collection apparatus and said biological agent identifier apparatus and used for reporting test results provided by said biological agent identifier apparatus.

2. The system according to claim 1 wherein said control is semi-automated control and the receptacle is manually transported from the concentrator apparatus to the biological agent identifier apparatus.

3. The system according to claim 2 wherein the biological agent identifier apparatus comprises a polymerase chain reaction (PCR) type bio-agent identifier apparatus.

4. The system according to claim 1 wherein the cartridge type receptacle comprises a polymerase chain reaction (PCR) cartridge.

5. The system according to claim 1 wherein the collection apparatus operates continuously to collect samples of particles.

6. The system according to claim 1 wherein the receptacle is manually transported to the biological agent identifier apparatus, and wherein the fluidics apparatus periodically delivers a portion of the liquid sample to said receptacle prior to the receptacle being manually transported to the biological agent identifier apparatus.

7. The system according to claim 1 wherein the biological agent identifier apparatus comprises a polymerase chain reaction (PCR) type bio-agent identifier apparatus.

8. The system according to claim 1 wherein the mail pinching apparatus includes a singulator and a dual belt mail transport assembly downstream of the singulator, and wherein the hood includes an elongated hood structure overlaying both singulator and the dual belt transport assembly.

9. The system according to claim 8 wherein the hood includes a pair of side panels on either side of the mail transport path and having cut-outs therein for the passage through of belts of the dual belt mail transport assembly.

10. The system according to claim 1 further includes a dry cyclone pre-separator and a wet-cyclone aerosol concentrator assembly.

11. The system according to claim 1 wherein the fluidics apparatus is capable of temporarily holding a sample in a reservoir which can be accessed for one or more analyses while the collection apparatus is collecting a next sample.

12. The system according to claim 1 wherein the fluidics apparatus additionally archives a remaining portion of the liquid sample.

13. The system according to claim 1 wherein the receptacle contains assay reagents for a single gene sequence of a target biological agent and an internal control.

14. The system according to claim 1 wherein the biological agent identifier apparatus comprises a single bay unit.

15. The system according to claim 1 wherein the control apparatus includes a local machine control computer controlling the operations of the biological agent identifier apparatus, the collection apparatus, the concentrator apparatus, and the fluidics apparatus.

16. The system according to claim 15 wherein the control apparatus additionally includes a site command and control computer connected to and controlling the local machine control computer as well as reporting the test results to a predetermined location.

17. The system according to claim 1 additionally includes an apparatus for housing the collection apparatus, the concentrator apparatus, the fluidics apparatus, and the biological agent identifier apparatus.

18. A biohazard detection system for detecting biological agents in a piece of mail fed along a mail transport path of a mail sorting apparatus, said biohazard detection system comprising:

a mail pinching apparatus located at a predetermined pinch point along said mail transport path and used for expelling aerosol particles including biological agents from said piece of mail;

a capturing and concentrating apparatus located at said pinch point and used for capturing aerosol particles expelled from said piece of mail at said pinch point and used for concentrating aerosol particles captured at said pinch point in a liquid sample;

a biological agent identifier apparatus; and a fluidics apparatus connected to said capturing and concentrating apparatus and used for feeding said liquid sample to said biological agent identifier apparatus.

19. The system according to claim 18 wherein the capturing and concentrating apparatus includes a particle collection device above the mail transport path at said pinch point.

20. The system according to claim 19 wherein the particle collection device includes a hood.

21. The system according to claim 18 wherein the mail pinching apparatus includes singulator apparatus for converting a non-singulated flow of pieces of mail to a singulated flow of mail and for pinching an individual piece of mail for causing expulsion of said aerosol particles.

22. The system according to claim 21 wherein the mail pinching apparatus additionally includes a pair of mail transporting belts downstream of the singulator apparatus such that the singlulated flow of mail is pinched and further possible expulsion of said aerosol particles is resulted.

23. The system according to claim 18 wherein the capturing and concentrating apparatus includes a particle collection device comprising a hood above the mail transport path at the pinch point; and wherein the mail pinching apparatus comprises a singulator apparatus and a pair of belts such that a single piece of mail is pinched thereby causing aerosol particle expulsion.

* * * * *